United States Patent [19]

Prasad et al.

[11] 4,228,279
[45] Oct. 14, 1980

[54] PRODUCTION OF O,O-DIALKYL-S-(BENZAZIMIDOMETHYL)-THIOLPHOSPHORIC ACID ESTERS

[75] Inventors: Vidyanatha A. Prasad, Overland Park, Kans.; James H. Vines, Kansas City, Mo.

[73] Assignee: Mobay Chemical Corporation, Pittsburgh, Pa.

[21] Appl. No.: 70,478

[22] Filed: Aug. 28, 1979

[51] Int. Cl.$^2$ .......................................... C07D 253/08
[52] U.S. Cl. ................................................... 544/183
[58] Field of Search ........................................ 544/183

[56] References Cited

U.S. PATENT DOCUMENTS

| | | | |
|---|---|---|---|
| 2,758,115 | 8/1956 | Lorenz | 544/183 |
| 3,420,829 | 1/1969 | Lorenz | 544/183 |
| 3,502,670 | 3/1970 | Rigterink | 544/183 |
| 3,551,562 | 12/1970 | Rigterink | 544/183 |
| 3,622,578 | 11/1971 | Rigterink | 544/183 |
| 3,845,053 | 10/1974 | Drabek | 544/183 |
| 3,876,638 | 4/1975 | Oswald | 544/183 |

FOREIGN PATENT DOCUMENTS

| | | |
|---|---|---|
| 927270 | 5/1955 | Fed. Rep. of Germany . |
| 44-16378 | 7/1969 | Japan . |
| 334531 | 1/1959 | Switzerland . |

*Primary Examiner*—John M. Ford
*Attorney, Agent, or Firm*—Sprung, Felfe, Horn, Lynch & Kramer

[57] ABSTRACT

In the reaction of a halomethylbenzazamide with an O,O-di-lower alkyl-thiolphosphoric acid ester to form an ester in accordance with the equation

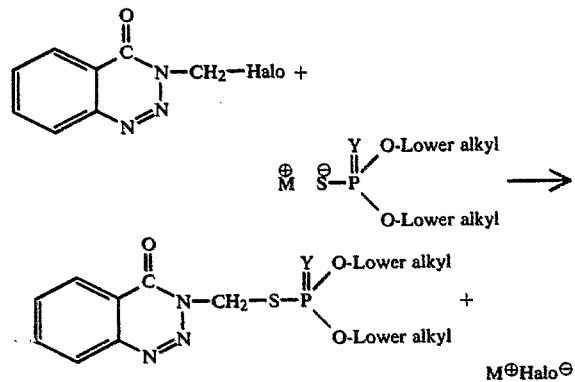

in which
  Y is oxygen or sulfur, and
  M is an alkali metal or ammonium cation,
the improvement which comprises starting the reaction at a pH from about 2.5 to 5.5, whereby the desired reaction product is produced in higher yield and assay.

6 Claims, No Drawings

PRODUCTION OF O,O-DIALKYL-S-(BENZAZIMIDOMETHYL)-THIOLPHOSPHORIC ACID ESTERS

The present invention relates to improvements in the production of O,O-dialkyl-S-(benzazimidomethyl)-thiol phosphoric acid esters.

U.S. Pat. No. 2,758,115 is directed to the production of O,O-dialkyl-S-(benzazimidomethyl)-thiol phosphoric acid esters in accordance with the following equation:

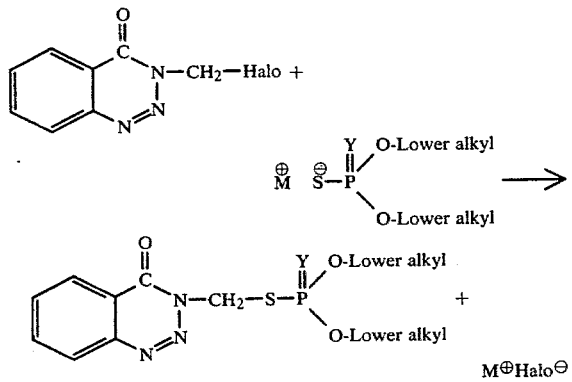

in which
Y is oxygen or sulfur,
M is an alkali metal or ammonium cation, and
Lower alkyl preferably has from 1 to 4 carbon atoms, especially methyl.

The compounds are highly effective insecticides, particularly that compound wherein Y is sulphur and the lower alkyl radicals are methyl. The product is obtained in high yield and in moderate purity but, in order to drive the reaction to completion, there is employed in the reaction a substantial excess of the salt of the dialkylthiolphosphoric acid. For example, a 25% excess is quite customary, the reactants being reacted in aqueous systems at alkaline pH's. For example, the sodium salt of the dialkylthiolphosphoric acid is produced by neturalization of the corresponding acid as with sodium hydroxide to a pH of 8–8.5 and the halomethylbenzazimide is reacted therewith. If the salt is permitted to stand for a few hours, the pH drops slightly and may even reach a value as low as 5.5–6 after some time but ordinarily the salt is used in freshly prepared form so the higher pH prevails. As noted, the process is quite satisfactory and the product has achieved substantial success. The excess salt employed in the process, however, must be disposed of and, because of its high phosphorus, sulphur and carbon contents, it imparts to the waste stream a high COD value.

Since there is considerable concern about reducing the impact on the environment, it is accordingly an object of the present invention to carry out the process in such manner that there is little or no pollution and reduced COD values of the waste stream.

It is a further object of the invention to be able to carry out the process without reduction in yield and/or assay but using a markedly diminished excess of the phosphorus and sulphur-containing starting material.

These objects are realized in accordance with the present invention pursuant to which the illustrated reaction is effected at a pH from about 5.5 to as low as 2.5, preferably about 2.5 to 3.5. In this manner both the yield and assay are improved compared to higher pH. Conversely, it is possible to achieve the same yield and assay heretofore available but with a markedly reduced excess of one of the starting materials, e.g. 15% or even as little as 10% excess compared with 25% or more in the prior art.

The reduced pH of the reaction can be achieved by the addition of an acid such as a mineral acid, e.g. a hydrogen halide acid, especially hydrochloric acid, to the reaction medium or initially to the dialkylthiolphosphoric acid ester salt.

The reaction is advantageously conducted in aqueous solution or suspension although organic solvents may be present. The temperature and other conditions of the reaction can be as the same heretofore employed, e.g. about 50° to 75° C. for several hours. At the end of the reaction there will be an organic phase containing the desired product and it can be separated from the aqueous layer and purified in conventional manner.

By operating in accordance with the invention it is routinely possible to obtain yields and assays in the region of 90% employing a conventional 25% excess of the phosphorus and sulphur-containing reactant and this can also be achieved at lower excesses.

In the interest of safety the reaction may be effected in a glass-lined reactor.

In the purification it is advantageous that no more caustic be used than necessary in order to clean the material since it may result in reduced yields.

It was attempted to improve the reaction efficiency through reduction of the excess dialkyl thiol phosphoric acid salt through use of a phase transfer catalyst such as benzyltriphenylphosphonium chloride, benzyltriethyl ammonium bromide, and the like. Surprisingly this did not improve the efficiency but had just the opposite effect, resulting in a drastic drop of assay, presumably due to partial decomposition of the starting material.

The invention will be further described in the following illustrative examples wherein all parts are by weight unless otherwise expressed.

EXAMPLE 1

A 40% solution of the sodium salt of O,O-dimethyl-dithiophosphoric acid ester was added in 10% stoichiometric excess to a 40% solution of chloromethylbenzazimide in ethylene dichloride with agitation and the pH was brought from 7 to 3.1 by addition of concentrated HCl; the 40% chloromethylbenzazimide solution was obtained by vacuum stripping of the necessary amount of solvent from a solution of 20.5% concentration. The temperature was raised to 65° C. and the mixture was held for 4½ hours at 62°–63° C. The reaction mixture was cooled to 35° C. and filtered to aid phase separation. No solids were noted on the filter paper. An organic layer separated from an aqueous layer which latter was discarded. 80 grams of a 1.5% NaOH solution was charged to a flask and the organic layer was added dropwise over a fifteen minute period to the caustic solution at 40° C. The pH at the end of the addition was 11.5. The mixture was agitated at 40° C. for half an hour. It was then filtered through a Buchner-funnel using 2 grams of a filter aid. The phases were separated. The organic phase was washed with 150 ml water. The phases were separated. The organic phase was dried and stripped on a rotary evaporator (40° C., approximately 75 mm Hg). The O,O-dimethyl-S-(benzazimidomethyl)-dithiophosphoric acid ester product was poured on a tared foil, air dried overnight, weighed and analyzed. Weight of Product: 76.25 g; theory: 79.3 g Crude Yield: 76.25/79.3 g=96.15% Assay: "as is" 91.3%; % solvent: 0.47%; dry: 91.7%

EXAMPLE 2

The process of Example 1 was repeated using a 25% excess of the ester but, instead of HCl, the pH was initially brought to 8.5 by addition of sodium bicarbonate. The yields and assay were comparable to Example 1.

EXAMPLE 3

The process of Example 2 was repeated except that there was only a 15% excess of the ester. There was a drop of 3-4% in assay and a similar drop in yield.

EXAMPLE 4

Substantially the same results as in Example 3 were obtained if the sodium bicarbonate was omitted, the pH of the solution upon standing falling from an initial value of 8 to 6.

EXAMPLE 5

The process of Example 1 was repeated three times on a larger scale using a 15% excess of the ester, the three runs giving products with an average assay on a dry basis of 93.1%.

In the table which follows there are set forth the parameters of various trials including Examples 1 to 5:

TABLE

| EX. | ASSAY, % CMB | ASSAY, % DMS | EXCESS DMS % | CONDENSATION pH | CRUDE YIELD BASED ON CMB, % | PRODUCT ASSAY DRY, % | NET YIELD, % CRUDE × ASSAY | NOTE |
|---|---|---|---|---|---|---|---|---|
| 1 | 19.1 | 40.6 | 10 | 3.0 | 96.1 | 91.5 | 87.8 | |
| 2 | 19.1 | 39.9 | 25 | 8-8.5 Na HCO$_3$ | 95.5 | 91 | 87.3 | |
| 3 | 19.1 | 39.9 | 15 | 8-8.5 Na HCO$_3$ | 93.4 | 86 | 80.1 | |
| 4 | 19.1 | 39.9 | 15 | started at 8, fell to 6 in 1 hr. | 95.4 | 87.8 | 82.9 | |
| 5a | 19.2 | 41.2 | 14 | 3.0 conc. HCl | 95.6 | 92.8 | 88.7 | |
| 5b | 19.2 | 41.2 | 14 | 3.0 conc. HCl | 96.1 | 92.2 | 88.6 | |
| 5c | 19.1 | 40.6 | 16 | 3.0 conc. HCl | 97.2 | 94.2 | 91.5 | |
| 6 | 18.6 | 39.2 | 25 | 8-8.5 Na HCO$_3$ | 94.5 | 92.5 | 87.2 | |
| 7 | 18.6 | 39.2 | 15 | 8-8.5 Na HCO$_3$ | 91.6 | 90.0 | 82.5 | |
| 8 | 18.6 | 39.2 | 15 | started at 8, fell to 6 in 1 hr. | 98.8 | 89.5 | 88.4 | |
| 9 | 18.5 | 40.9 | 25 | started at 8, fell to 6 in 1 hr. | | | | |
| 10 | 18.5 | 40.9 | 25 | 8-8.5 Na HCO$_3$ | 99 | 92 | 91.1 | |
| 11 | 19.1 | 40.2 | 15 | started at 8, fell to 6 in 1 hr. | 94.5 | 88.5 | 83.6 | |
| 12 | 19.1 | 40.2 | 25 | 8-8.5 Na HCO$_3$ | 96.1 | 92.8 | 89.1 | |
| 13 | 19.1 | 40.6 | 25 | 3.6 | 94.5 | 94 | 87.9 | |
| 14 | 19.1 | 40.6 | 25 | 8-8.5 Na HCO$_3$ | 95.6 | 91.5 | 87.0 | |
| 15 | 19.1 | 40.6 | 10 | 3.6 | 97.2 | 90.8 | 88.1 | a |
| 16 | 19.1 | 40.6 | 10 | 3.6 | 93 | 0.6 | 84.1 | b |
| 17 | 19.1 | 41.2 | 25 | 8-8.5 Na HCO$_3$ | 95.2 | 92.3 | 87.6 | a |
| 18 | 19.1 | 41.2 | 15 | 3.1 | 97.3 | 92.0 | 89.0 | a |
| 19 | 19.5 | 39.2 | 15 | 3.5 | 96.8 | 90.2 | 87.3 | |
| 20 | 19.5 | 39.2 | 25 | 8-8.5 Na HCO$_3$ | 95.7 | 90.1 | 86.2 | |
| 21 | 20.5 | 39.2 | 25 | 8-8.5 Na HCO$_5$ | 88.6 | 92.0 | 81.9 | c |
| 22 | 20.5 | 39.2 | 10 | 2.5 | 90.1 | 91.6 | 82.4 | c |
| 23 | 18.8 | 43.8 | 25 | 8-8.5 Na HCO$_3$ | 98.8 | 92.3 | 91.2 | |
| 24 | 18.8 | 43.8 | 12.5 | 3.1 | 10 | 92.8 | 92.8 | |

NOTES:
a Caustic wash 0.5 hr. at 40° C. to pH 11.
b Caustic wash at 60° C.
c Believe slight error in initial CMB assay since crude and net yields should be slightly higher.

It will be appreciated that the instant specification and examples are set forth by way of illustration and not limitation, and that various modifications and changes may be made without departing from the spirit and scope of the present invention.

What is claimed is:

1. In the reaction of a halomethylbenzazamide with an 0,0-di-lower alkyl-thiolphosphoric acid ester to form an ester in accordance with the equation

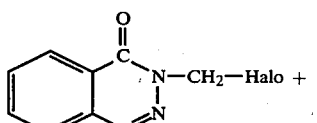

-continued

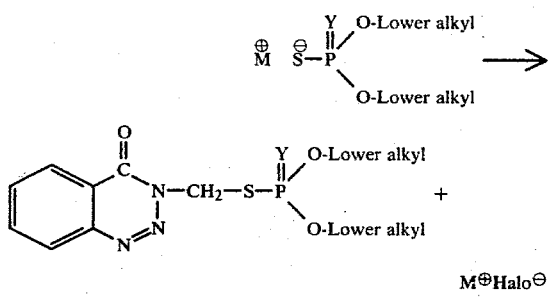

in which

Y is oxygen or sulfur, and

M is an alkali metal or ammonium cation, the improvement which comprises starting the reaction at a pH from about 2.5 to 5.5, whereby the desired reaction product is produced in higher yield and assay.

2. A process according to claim 1, wherein Y is sulfur, Lower alkyl is methyl, Halo is chloro, and M is sodium.

3. A process according to claim 1, wherein the reaction is initiated at a pH from about 2.5 to 3.5.

4. A process according to claim 1, wherein the starting thiolphosphoric acid ester is present in no more than about a 15% stoichiometric excess.

5. A process according to claim 2, wherein the reaction is initiated at a pH from about 2.5 to 3.5 by addition of an acid to an aqueous solution of the reactants wherein the starting thiolphosphoric acid ester is present in no more than about a 15% stoichiometric excess.

6. A process according to claim 5, wherein the acid is HCl.

* * * * *